United States Patent [19]

Minami et al.

[11] Patent Number: 5,334,484
[45] Date of Patent: Aug. 2, 1994

[54] PHOTOPOLYMERIZABLE COMPOSITION AND PHOTOPOLYMERIZABLE ELEMENT

[75] Inventors: Yoshitaka Minami; Hajime Kakumaru, both of Hitachi; Naohiro Kubota, Urawa; Nobuhide Tominaga, Urawa; Koji Ishizaki, Urawa, all of Japan

[73] Assignees: Hitachi Chemical Co., Ltd.; Asahi Denka Kogyo Kabushiki Kaisha, both of Tokyo, Japan

[21] Appl. No.: 859,430

[22] PCT Filed: Sep. 27, 1991

[86] PCT No.: PCT/JP91/01293
§ 371 Date: Jun. 15, 1992
§ 102(e) Date: Jun. 15, 1992

[87] PCT Pub. No.: WO92/06412
PCT Pub. Date: Apr. 16, 1992

[30] Foreign Application Priority Data

Sep. 28, 1990 [JP] Japan .................. 2-260876

[51] Int. Cl.⁵ .................. G03C 1/73; G03F 7/031
[52] U.S. Cl. .................. 430/281; 430/916; 430/920; 430/271; 522/50; 522/63
[58] Field of Search .......... 430/281, 920, 916, 271; 522/50, 63; 546/102, 103

[56] References Cited

U.S. PATENT DOCUMENTS 5,045,433  9/1991  Kakumaru et al. ............... 430/281
5,089,377  2/1992  Kakumaru et al. ............... 430/281

FOREIGN PATENT DOCUMENTS 53-27605   8/1978  Japan .
59-226002 12/1984  Japan .
60-164739  8/1985  Japan .
63-256602 10/1988  Japan .
2-69463    3/1990  Japan .
2-226148   9/1990  Japan .

OTHER PUBLICATIONS

Chemical Abstracts 11th Collective Index vols. 96–105 1982–1986 p. 19104F.
Hsu et al. Journal of Polymer Science, vol. 22 (Nov. 1984) p. 2873.
Code of Federal Regulations #21 parts 170 to 199 revised as of Apr. 1, 1993 p. 337 (Food & Drug Administration, HHS).
Grant & Hackh's Chemical Dictionary, 5th Edition 1987 pp. 415, 560, 587.
Chemical Abstract CA82(5):31238f of Torii et al. Heterocycles, 2(5), 615–20 (1974).

Primary Examiner—Janis L. Dote
Attorney, Agent, or Firm—Young & Thompson

[57] ABSTRACT

A photopolymerizable composition comprising: (a) 100 parts by weight of a compound having at least one ethylenically unsaturated group, (b) 0 to 400 parts by weight of a thermoplastic organic polymer and (c) 0.01 to 20 parts by weight of a photoinitiator, characterized in that an acridine compound of the following general formula (I) is used as the photoinitiator:

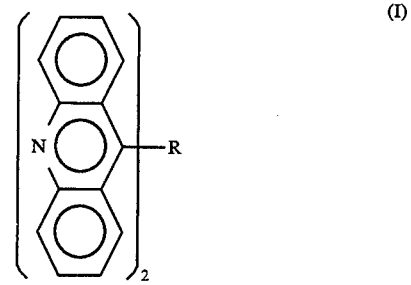

wherein R represents an alkylene, oxadialkylene or thiodialkylene group having 2 to 20 carbon atoms, and a photopolymerizable element comprising a layer of the photopolymerizable composition formed on a support.

3 Claims, No Drawings

PHOTOPOLYMERIZABLE COMPOSITION AND PHOTOPOLYMERIZABLE ELEMENT

TECHNICAL FIELD

The present invention relates to a photopolymerizable composition and a photopolymerizable element. In particular, the present invention relates to a photopolymerizable composition having an improved photosensitivity and a photopolymerizable element produced therefrom.

BACKGROUND ART

It is advantageous to increase the polymerization rate of a photopolymerizable composition, namely to increase the photosensitivity of the photopolymerizable composition, for shortening the time of exposure to an actinic radiation. Various processes have been proposed for this purpose from old times.

For example, a photoinitiator or photosensitizer is added to a photopolymerizable composition comprising an ethylenically unsaturated compound in order to improve the photosensitivity thereof. The photoinitiators or photosensitizers thus used include polynuclear quinones such as 2-ethylanthraquinone and 2-tert-butylanthraquinone, aromatic ketones such as benzophenone and 4,4'-bis (dimethylamino)benzophenone, and benzoin derivatives such as benzoin methyl ether.

However, the photosensitivity of the ordinary photopolymerizable composition containing such a photoinitiator or photosensitizer is not always sufficient.

Japanese Patent Publication No. 27605/1978 discloses an acridine or phenazine compound which may contain a condensed benzene ring as a photoinitiator having a high sensitivity particularly in the presence of oxygen and an excellent storability. Japanese Patent Laid-Open No. 226002/1984 discloses a combination of 9-phenylacridine with a thiol compound as a photoinitiator having a high sensitivity. Japanese Patent Laid-Open No. 164739/1985 discloses a substituted 9-benzoylacridine as a photoinitiator having a high sensitivity. However, no photopolymerizable composition having a satisfactory photosensitivity could be obtained even by using such a compound used heretofore.

Therefore, an object of the present invention it to provide a new photopolymerizable composition having an improved photosensitivity and a photopolymerizable element prepared therefrom by overcoming the defects of the prior art.

DISCLOSURE OF THE INVENTION

The inventors have found that the above-described object can be attained by using a composition comprising an ethylenically unsaturated compound and containing, as a photoinitiator, a specified bisacridine compound having two acridyl groups in the molecule. The present invention has been completed on the basis of this finding.

Thus the present invention relates to a photopolymerizable composition comprising:

(a) 100 parts by weight of a compound having at least one ethylenically unsaturated group, (b) 0 to 400 parts by weight of a thermoplastic organic polymer, and (c) 0.01 to 20 parts by weight of a photoinitiator, characterized in that an acridine compound of the following general formula (I) is used as the photoinitiator:

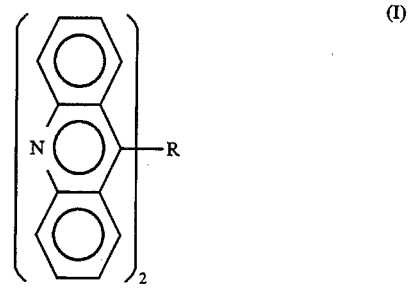

wherein R represents an alkylene, oxadialkylene or thiodialkylene group having 2 to 20 carbon atoms, and a photopolymerizable element comprising a layer of the photopolymerizable composition formed on a support.

In the acridine compounds of the above general formula (I), those wherein R represents an alkylene group having 6 to 12 carbon atoms are particularly useful, novel compounds.

DETAILED DESCRIPTION OF THE INVENTION

A detailed description will be made on the present invention.

The compounds (a) having at least one ethylenically unsaturated group in the photopolymerizable composition of the present invention include compounds obtained by adding an α, β-unsaturated carboxylic acid to a polyhydric alcohol, such as tetraethylene glycol di(meth)acrylate [(meth)acrylate meaning either methacrylate or acrylate], polyethylene glycol di(meth)acrylate (having 2 to 14 ethylene groups), trimethylolpropane di(meth)acrylate, trimethylolpropane tri(meth)acrylate, pentaerythritol tri(meth)acrylate, pentaerythritol tetra (meth)acrylate, polypropylene glycol di(meth)acrylate, (having 2 to 14 propylene groups), dipentaerythritol penta(meth)acrylate and dipentaerythritol hexa (meth)acrylate; compounds obtained by adding an α,β-unsaturated carboxylic acid to a glycidyl compound, such as trimethylolpropane triglycidyl ether triacrylate and bisphenol A diglycidyl ether diacrylate; esters of a polycarboxylic acid such as phthalic anhydride with a substance having a hydroxyl group and an ethylenically unsaturated group, such as β-hydroxyethyl (meth)acrylate; alkyl esters of acrylic or methacrylic acid, such as methyl (meth)acrylate, ethyl (meth)acrylate, butyl (meth)acrylate and 2-ethylhexyl (meth)acrylate. The components (a) contained in the photopolymerizable composition of the present invention include also reaction products of a compound having at least one isocyanate group, such as toluene diisocyanate, trimethylhexamethylene diisocyanate, diphenyl diisocyanate, diphenylmethane diisocyanate or 3,3'-dimethyl-4,4'-diphenyl diisocyanate, with a compound having at least one hydroxyl group and at least one ethylenically unsaturated group, such as β-hydroxyethyl (meth)acrylate, vinyl alcohol, trimethylolpropane di(meth)acrylate, pentaerythritol tri(meth)acrylate and diethylene glycol mono(meth)acrylate.

From the viewpoints of odor and safety, the boiling point of the component (a) is preferably at least 100° C. under an atmospheric pressure.

The amount of the component (a) is 100 parts by weight.

The thermoplastic organic polymers [component (b)] include copolymers of an alkyl (meth)acrylate with (meth)acrylic acid and copolymers of an alkyl (meth)acrylate, (meth)acrylic acid and a vinyl monomer copolymerizable with them. The alkyl (meth)acrylates include methyl (meth)acrylate, ethyl (meth)acrylate, butyl (meth)acrylate and 2-ethylhexyl (meth)acrylate. The vinyl monomers copolymerizable with the alkyl (meth)acrylate or (meth)acrylic acid include tetrahydrofurfuryl (meth)acrylate, ethylene glycol di(meth)acrylate, glycidyl (meth)acrylate, 2,2,2-trifluoroethyl (meth)acrylate, 2,2,3,3-tetrafluoropropyl (meth)acrylate, acrylamide, diacetone acrylamide, styrene and vinyltoluene. The thermoplastic organic polymers include the homopolymers of the above-described compounds as well as copolyesters, such as polyesters of terephthalic acid, isophthalic acid and sebacic acid, butadiene/acrylonitrile copolymer, cellulose acetate, cellulose acetate butyrate, methylcellulose and ethylcellulose.

The amount of the thermoplastic organic polymer is 0 to 400 parts by weight, preferably 20 to 250 parts by weight. By using the thermoplastic organic polymer, the film forming properties and the toughness of the hardened film can be improved. When the amount thereof exceeds 400 parts by weight, the relative amounts of the other components become smaller and, therefore, the photosensitivity is reduced. From the viewpoints of the film forming properties and the toughness of the film, the weight-average molecular weight of the thermoplastic organic polymer is preferably in the range of 10,000 to 1,000,000, still preferably 10,000 to 150,000.

The acridine compounds of the above general formula (I) are used as the photoinitiator [component (c)] of the present invention. The acridine compounds of the above general formula (I) include 1,2-bis (9-acridinyl)ethane, 1,3-bis (9-acridinyl)propane, 1,4-bis (9-acridinyl)butane, 1,6-bis (9-acridinyl)hexane, 1,7-bis(9-acridinyl)heptane, 1,8-bis (9-acridinyl)octane, 1,9-bis-(9-acridinyl)nonane, 1,10-bis (9-acridinyl)decane, 1,11-bis (9-acridinyl)undecane, 1,12-bis (9-acridinyl)dodecane, 1,14-bis (9-acridinyl)tetradecane, 1,16-bis(9-acridinyl)hexadecane, 1,18-bis (9-acridinyl)octadecane, 1,20-bis (9-acridinyl)eicosane, 1,3-bis (9-acridinyl)-2-oxapropane, and 1,5-bis (9-acridinyl)-(9-acrid octadecane, 1,20-bis (9-acridinyl)eicosane, 1,3-bis (9-acridinyl)-2-oxapropane, and 1,5-bis (9-acridinyl)-2-thiapropane and 3-thiapentane. Among these compounds, those wherein the alkylene group [R in the general formula (I)] bonding the two acridine rings together has 6 to 12 carbon atoms are preferred from the viewpoint of photosensitivity.

The acridine compounds of the above general formula (I) can be easily produced by, for example, reacting diphenylamine with a dicarboxylic acid in the presence of a metal chloride.

The compounds of the general formula (I) of the present invention produced as described above can be used alone as the photoinitiator having a remarkable effect and, in addition, they can be used also in combination with another well-known photoinitiator.

The photoinitiator [component (c)] of the present invention is used in an amount of 0.01 to 20 parts by weight, preferably 0.1 to 10 parts by weight, for 100 parts by weight of the component (a).

When the amount of the photoinitiator is below 0.01 part by weight, no sufficient photosensitization can be expected and, therefore, the photopolymerization does not sufficiently proceed. On the contrary, when it exceeds 20 parts by weight, the storability of the photopolymerizable composition is poor and impractical.

The photoinitiator [component (c)] used in the present invention may be a combination of two or more of them or it can be used in combination with various other organic amine compounds and organic sulfur compounds.

The organic amine compounds include triethanolamine, triisopropanolamine, methyldiethanolamine, octyldiethanolamine, octadecyldiethanolamine, dibutylethanolamine, dioctylethanolamine, diethanolaniline, diethanolamine, methylethanolamine, butylethanolamine, tetrahydroxyethylethylenediamine, tetrahydroxyethylhexamethylenediamine, triethylamine, tributylamine, dimethylaminopropylamine, dimethylaniline, 4-dimethylaminotoiuene, 4-diethylaminotoluene, 4-dimethylaminocyanobenzene, 4-diethylaminocyanobenzene, 4-dimethylaminobromobenzene, 4-diethylaminobromobenzene, 4-dimethylaminonitrobenzene, 4-diethylaminonitrobenzene, alkyl 4-dimethylaminobenzoates, alkyl 4-diethylaminobenzoates, 4-dimethylaminopyridine, 4-diethylaminopyridine, 4-pyrrolidinopyridine, phenylglycine, diethylaniline, diethylamine, dioctylamine, tetramethylethylenediamine, Michler's ketone and anthranilic acid.

The organic sulfur compounds include 2-mercaptoimidazole, 2-mercaptooxazole, 2-mercaptothiazole, 2-mercaptobenzimidazole, 2-mercaptobenzoxazole, 2-mercaptobenzothiazole, 6-chloro-2-mercaptobenzimidazole, 5-methylmercapto-1-phenyltetrazole, 6-methoxy-2-mercaptobenzimidazole, 2-mercaptonaphthimidazol, 2-mercaptonaphthoxazole and 3-mercapto-1,2,4-triazole.

The photopolymerizable composition of the present invention may contain a thermal polymerization inhibitor such as p-methoxyphenol, hydroquinone, pyrogallol, naphthylamine, phenothiazine or t-butylcatechol.

The photopolymerizable composition of the present invention may contain a colorant such as a dye or pigment. The colorants usable herein include Fuchsine, Auramine base, Crystal Violet, Victoria Pure Blue, Malachite Green, Methyl Orange and Acid Violet RRH.

Further the photopolymerizable composition of the present invention may contain known additives such as plasticizers, adhesion accelerators and talc, as well as a combination of a halogen compound such as carbon tetrabromide with a leuco dye in order to change the color of the exposed part.

The photopolymerizable composition of the present invention can be used in the form of a solution or an aqueous solution thereof prepared by dissolving, mixing or dispersing the above-described components in, for example, acetone, methyl ethyl ketone, methyl isobutyl ketone, methyl Cellosolve, ethyl Cellosolve, chloroform, methylene chloride, methyl alcohol, ethyl alcohol, aqueous ammonia or water or, alternatively, in the form of a solventless solution thereof prepared by dissolving the components other than the compound (a) having an ethylenically unsaturate group in the compound (a) without using any solvent or dispersing medium.

The composition may be directly applied to a base material such as a copper, aluminum, ceramic or plastic plate by the known printing, immersion or electrodeposition method such as the roll coater, curtain coater, spray coating or screen printing method. Alternatively, the composition may be applied to the base material after applying it to a support such as a polyester film, removing the solvent or dispersion medium, if present, by drying to form a photopolymerizable composition layer on the support and, if necessary, placing a polyolefin film such as a polyethylene film thereon as a protective film to form a photopolymerizable element. The preparation method is thus not particularly limited.

The photopolymerizable composition of the present invention can be used as the material of various substances such as photosetting paints, photosetting inks, photosensitive printing plates, photoresists, dry films and electrodeposited photoresists. The use thereof is not particularly limited. For example, it is used as a photoresist for printed wiring boards by applying the photopolymerizable composition in solution form to a base material such as a copper plate, drying it when it contains a solvent, and exposing it to an actinic radiation to effect photosetting. Alternatively, it is used by applying the photopolymerizable composition in solution form to a polyethylene terephthalate film, drying it when it contains a solvent, placing the film on a base material to form a laminate and photosetting. The sources of the actinic radiation usable for the photosetting are those emitting a light of a wavelength of 300 to 450 nm, such as mercury vapor arc, carbon arc and xenone arc.

The following Examples will further illustrate the present invention, which by no means limit the invention.

An example of the synthesis of the acridine compound of the above general formula (I) usable in the present invention will be given below.

SYNTHESIS EXAMPLE 1

Preparation of 1,7-bis (9-acridinyl)heptane

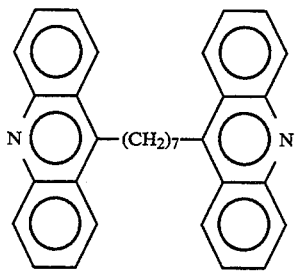

18.8 g (0.1 mol) of azelaic acid, 102 g (0.75 mol) of anhydrous zinc chloride and 33.8 g of diphenylamine were put in a 500-ml three-necked flask provided with a thermometer, hermetically sealed stirred water separator and condenser and stirred at 220° to 230° C. for 20 h.

After cooling to 100° C., 200 ml of hot water was slowly added thereto. Then 150 ml of 30% sulfuric acid was added thereto at that temperature and the mixture was cooled under stirring to precipitate a reaction mixture in the form of dark brown grains, which were separated by filtration and dispersed in 200 ml of toluene, and 200 ml of 28% aqueous ammonia was added thereto.

The toluene layer was separated and thoroughly washed with warm water. 100 ml of toluene was distilled off under reduced pressure and the residue was cooled to precipitate the product, which was separated by filtration to obtain 12 g (yield: 27%) of the product in the form of a white powder having a melting point of 153° to 157° C.

The results of nuclear magnetic resonance analysis were as follows, from which the product was confirmed to be the intended compound:

| | |
|---|---|
| —$CH_2$—: | 1.5 to 2.7 ppm (br 10 H) |
| —$CH_2$— adjacent to aromatic nucleus: | |
| | 3.8 to 4.2 ppm (t 4 H) |
| aromatic nucleus: | 6.8 to 8.8 ppm (m 16 H) |

The following compounds were synthesized in the same manner as that described above except that azelaic acid was replaced by other dicarboxylic acids:

| Carboxylic acid | Product | M.P. (°C.) |
|---|---|---|
| Sebacic acid | 1,8-bis(9-acridinyl)-octane | 196 |
| Brassylic acid | 1,11-bis(9-acridinyl)-undecane | 103 |

EXAMPLE 1

248.8 g of a solution containing 93.3 g of nonvolatile matter was prepared by mixing 52 g of a methyl methacrylate/methacrylic acid/2-ethylhexyl methacrylate (weight ratio: 60/20/20) copolymer (weight-average molecular weight: 80,000), 10 g of tetraethylene glycol diacrylate, 30 g of poly(P≈5)oxyethylene bisphenol A dimethacrylate (BPE-10 mfd. by Shin-Nakamura Chemical Co., Ltd.), 0.2 g of Malachite Green, 0.1 g of hydroquinone, 1.0 g of Leucocrystal Violet, 0.5 g of carbon tetrabromide, 10 g of toluene, 130 g of methyl Cellosolve, 5 g of methyl alcohol and 10 g of chloroform.

Each photoinitiator listed in Table 1 was dissolved in the solution to obtain a solution of a photopolymerizable composition.

Then the solution of the photopolymerizable composition was evenly applied to a polyethylene terephthalate film having a thickness of 25 μm and dried in a hot air convection dryer at 100° C. for 5 min to obtain a photopolymerizable element. The thickness of the layer of the photopolymerizable composition after drying was 25 μm.

Separately, the copper surface of a copper-clad laminate comprising a glass epoxy material having a copper foil having a thickness of 35 μm on both surfaces thereof (MCL-E-61 mfd. by Hitachi Chemical Co., Ltd.)was abraded with a #800 sand paper, washed with water and dried in air stream. The copper-clad laminate thus obtained was heated to 60° C. and the photopolymerizable element prepares as described above was placed thereon under heating at 120° C. to form a laminate.

The base thus formed was exposed to a light from 3-kW high pressure mercury arc lamp (Phenix-3000 mfd. by Oak Seisakusho) (40 mJ/$cm^2$) by using a negative film having an optical transmission reduced stepwise (step tablet having an optical density in the first step of 0.05, the optical density being increased by 0.15 in each step) in order to evaluate the photosensitivity.

After the exposure, the polyethylene terephthalate film was removed and a 2% aqueous sodium carbonate solution was sprayed on the remaining layer at 30° C. for 50 sec to remove the unexposed part.

By measuring the number of steps of the step tablet of the photoset film formed on the copper-clad laminate, the photosensitivity of the photopolymerizable composition was evaluated. The results are given in Table 1. The larger the number of the steps of the step tablet, the higher the photosensitivity.

TABLE 1

| No. | Photoinitiator | Amt.*1 | No. of steps |
|---|---|---|---|
| Ex. | | | |
| 1-1 | 1,7-bis(9-acridinyl)heptane | 0.5 | 7 |
| 1-2 | " | 0.7 | 9 |
| 1-3 | " | 1.0 | 10 |
| 1-4 | " | 0.7 | 7 |
| | Michler's ketone | 0.1 | |
| 1-5 | 1,8-bis(9-acridinyl)octane | 0.7 | 9 |
| 1-6 | 1,11-bis(9-acridinyl)undecane | 0.7 | 8 |
| Comp. Ex. | | | |
| 1-1 | benzophenone | 4.0 | 3 |
| | Michler's ketone | 0.17 | |
| 1-2 | benzophenone | 6.0 | 4 |
| | Michler's ketone | 0.17 | |
| 1-3 | benzophenone | 8.0 | 4 |
| | Michler's ketone | 0.17 | |
| 1-4 | 9-phenylacridine | 1.0 | 5 |
| 1-5 | 9-phenylacridine | 2.0 | 6 |

*1grams for 248.8 g of the solution
*2parts by weight for 100 parts by weight of component (b)

EXAMPLE 2

The following compounds were mixed together in the same manner as that of the Example 1 to obtain a photopolymerizable element having a photosensitive layer having a thickness of 75 μm; 43 g of a methyl methacrylate/methacrylic acid/ethyl acrylate (weight ratio: 50/20/30) copolymer (weight-average molecular weight≈80,000), 57 g of a reaction product of trimethylhexamethylene diisocyanate, 1,4-cyclohexanedimethanol and 2-hydroxyethyl acrylate (equivalent ratio: 16/5/8), 0.7 g of a photoinitiator, 0.1 g of p-methoxyphenol, 0.05 g of Victoria Pure Blue, 0.3 g of 5-amino-1,3,4-thiadiazole-2-thiol, 2.0 g of antimony trioxide, 30 g of propylene glycol monomethyl ether and 70 g of methyl ethyl ketone.

Then the element was applied to the copper surface of the copper-clad laminate with a commercially available vacuum laminator while the polyethylene terephthalate film was peeled off. After the exposure (250 mJ/cm$^2$) followed by the development for 200 sec the number of the steps of the step tablet of the obtained photoset film was determined.

For comparison, a photoset film was formed in the same manner as that described above except that the photoinitiator of the present invention was replaced by 5 g of benzophenone and 0.2 g of Michler's ketone to determine the number of the steps of the step tablet.

The results are given in Table 2.

The laminate having the photoset film formed by using the photoinitiator of the present invention was immersed in a molten solder at 260° C. for 10 sec. The photoset film was not peeled off from the copper and thus excellent properties of the solder mask were exhibited.

TABLE 2

| No. | Photoinitiator | Amt.*3 | No. of steps |
|---|---|---|---|
| Ex. | | | |
| 2-1 | 1,7-bis(9-acridinyl)heptane | 1.23 | 8 |
| 2-2 | 1,8-bis(9-acridinyl)octane | 1.23 | 8 |
| 2-3 | 1,11-bis(9-acridinyl)undecane | 1.23 | 7 |
| Comp. Ex. | | | |
| 2-1 | benzophenone (5 g) | 8.77 | 2 |
| | Michler's ketone (0.2 g) | 0.35 | |

*3parts by weight for 100 parts by weight of component (b)

EXAMPLE 3

A reaction product of 236 g of o-cresol novolak epoxy resin with 18 g of acrylic acid was reacted with 51 g of isocyanatoethyl methacrylate. The reaction product thus obtained was dissolved in 2-ethoxyethyl acetate to obtain a solution having a solid content of 68% by weight.

103.8 g (solid content: 70.6 g) of the 2-ethoxyethyl acetate solution was mixed with 35.6 g of silica, 7.1 g of talc, 2.0 g of antimony trioxide, 1 g of a photoinitiator, 16.7 g of ethoxyethyl acetate and 3.7 g of Phthalocyanine Green (TY-50323 mfd. by Toyo Ink Mfg. Co., Ltd.). The mixture was applied to the copper-clad laminate and dried in the same manner as that of the Example 1 to obtain a photopolymerizable composition layer having a thickness of 20 μm.

After the exposure (600 mJ/cm$^2$) followed by the development for 30 sec, the number of the steps of the step tablet of the obtained photoset film was determined.

For comparison, a photoset film was formed in the same manner as that described above except that the photoinitiator of the present invention was replaced with 1 g of 9-phenylacridine or 5 9 of 2-ethylanthraquinone and the number of the steps of the step tablet was determined.

The results are given in Table 3.

The laminate having the photoset film formed by using the photoinitiator of the present invention was immersed in a molten solder at 260° C. for 30 sec. The photoset film was not peeled off from the copper and thus excellent properties of the solder mask were exhibited.

TABLE 3

| No. | Photoinitiator | Amt.*4 | No. of steps |
|---|---|---|---|
| Ex. | | | |
| 3-1 | 1,7-bis(9-acridinyl)heptane | 1.42 | 7 |
| 3-2 | 1,8-bis(9-acridinyl)octane | 1.42 | 7 |
| 3-3 | 1,11-bis(9-acridinyl)undecane | 1.42 | 7 |
| Comp. Ex. | | | |
| 3-1 | 9-phenylacridine | 1.42 | 4 |
| 3-2 | 2-ethylanthraquinone (5 g) | 7.08 | 3 |

It is apparent from the results obtained in the above Examples that the photopolymerizable composition of the present invention containing the bisacridine compound has a far higher photosensitivity and more excellent solder masking properties than those of the photosensitive compositions containing a known photoinitiator such as 9-phenylacridine, a combination of benzophenone with Michler's ketone or 2-ethylanthraquinone.

Industrial Applicability

The photopolymerizable composition and photopolymerizable element prepared therefrom according to the present invention have a very high photosensitivity and when they are used for forming a photoresist, excellent resolution and line shape can be obtained and the contamination of the developer and the plating bath is only slight.

The photoset films formed by photosetting them have very excellent mechanical properties such as durability to soldering and plating, adhesion and tending.

Further, since the cold flow of the photopolymerizable composition of the present invention is low, a roll-shaped photosensitive element produced therefrom is substantially free from oozing-out at the end thereof and has an excellent storability.

We claim:
1. A photopolymerizable composition comprising:
   (a) 100 parts by weight of a compound having at least one ethylenically unsaturated group,
   (b) 0 to 400 parts by weight of a thermoplastic organic polymer and
   (c) 0.01 to 20 parts by weight of a photoinitiator, characterized in that an acridine compound of the following general formula (I) is used as the photoinitiator (c):

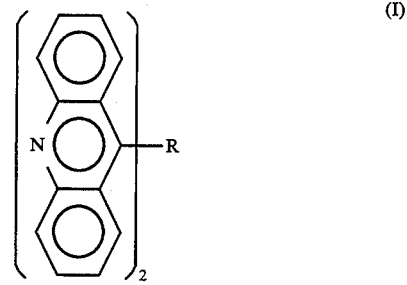

wherein R represents an alkylene, oxadialkylene or thiodialkylene group having 2 to 20 carbon atoms.

2. A photopolymerizable composition according to claim 1, wherein R in the general formula (I) of the photoinitiator (c) is an alkylene group having 6 to 12 carbon atoms.

3. A photopolymerizable element comprising a layer of the photopolymerizable composition according to claim 1 formed on a support.

* * * * *